United States Patent
Cunningham

[11] Patent Number: 5,326,449
[45] Date of Patent: Jul. 5, 1994

[54] COMPOSITE MEMBRANE
[75] Inventor: David D. Cunningham, Lakemoor, Ill.
[73] Assignee: Abbott Laboratories, Abbott Park, Ill.
[21] Appl. No.: 109,105
[22] Filed: Aug. 19, 1993

Related U.S. Application Data

[63] Continuation of Ser. No. 896,223, Jun. 10, 1992, abandoned, which is a continuation-in-part of Ser. No. 815,426, Dec. 31, 1991, abandoned.

[51] Int. Cl.$^5$ .............................................. G01N 27/26
[52] U.S. Cl. .................................. 204/403; 204/414; 204/415; 204/416; 204/418; 435/817; 435/288
[58] Field of Search ............... 204/403, 414, 415, 416, 204/418, 153.12; 435/817, 288

[56] References Cited

U.S. PATENT DOCUMENTS

| | | | |
|---|---|---|---|
| 3,797,274 | 3/1974 | Shimanckas | 64/16 |
| 3,835,014 | 10/1974 | Huffkines, Jr. | 204/415 |
| 4,073,713 | 2/1978 | Newman | 204/415 |
| 4,240,889 | 12/1980 | Yoda et al. | 204/415 |
| 4,276,141 | 6/1981 | Hawkins | 204/1 T |
| 4,321,123 | 3/1982 | Nakamura et al. | 204/403 |
| 4,376,689 | 3/1983 | Nakamura et al. | 204/403 |
| 4,388,166 | 6/1983 | Suzuki et al. | 204/403 |
| 4,415,666 | 11/1983 | D'Orazio et al. | 204/403 |
| 4,454,007 | 6/1984 | Pace | 204/416 |
| 4,486,292 | 12/1984 | Blackburn | 204/416 |
| 4,549,951 | 10/1985 | Knudson et al. | 204/416 |
| 4,579,642 | 4/1986 | Niiyama et al. | 204/403 |
| 4,759,828 | 7/1988 | Young et al. | 204/403 |
| 4,808,529 | 2/1989 | Doppelfeld et al. | 435/179 |
| 4,889,612 | 2/1989 | Geist et al. | 204/416 |
| 4,894,339 | 1/1990 | Hanazato et al. | 204/403 |
| 4,895,806 | 1/1990 | Le et al. | 435/288 |
| 4,909,908 | 3/1990 | Ross et al. | 204/403 |
| 4,923,586 | 5/1990 | Katayama et al. | 204/403 |

FOREIGN PATENT DOCUMENTS

| | | |
|---|---|---|
| 2003275 | 3/1979 | United Kingdom . |
| 2194843A | 3/1988 | United Kingdom . |

Primary Examiner—John Niebling
Assistant Examiner—Bruce F. Bell
Attorney, Agent, or Firm—Robert E. Wexler

[57] ABSTRACT

A sensor device for measuring the concentration of an analyte in solution is described. The device includes a composite membrane which incorporates a porous membrane containing an immobilized biologically-active protein and at least one other membrane. The other membrane may optionally be a blocking membrane, partly embedded in the porous membrane, which is adapted to exclude low molecular weight interfering species such as ascorbic acid. The other membrane may optionally be a protecting membrane which is useful for preventing high molecular species from fouling the porous membrane. Both a blocking membrane and a protecting membrane may be included in the composite membrane, simultaneously. The composite membrane is attached and reliably sealed to a housing by means of ultrasonic welding.

These features operate synergistically so that the device exhibits relatively fast response and recovery times, is reliably leak-proof, and may be constructed in relatively small sizes. A method of manufacturing the composite membrane is also provided.

18 Claims, 4 Drawing Sheets

COMPOSITE MEMBRANE

This application is a continuation of application Ser. No. 07/896,223, filed Jun. 10, 1992, now abandoned which is a continuation-in-part of application Ser. No. 815,426, filed Dec. 31, 1991, now abandoned.

FIELD OF THE INVENTION

The invention relates generally to a sensor for electrochemical analysis of a catalyzed reagent in solution. More particularly, the invention relates to a sensor having a composite membrane that contains a catalytic immobilized protein for converting a reagent to be measured into a product which can be detected electrically.

BACKGROUND OF THE INVENTION

Biosensors are electrodes which employ biologically active materials, usually proteins, as highly selective catalysts. Enzymes and antibodies are sub-classes of proteins. Early biosensors contained an enzyme in aqueous solution which was held in proximity to a sensing electrode by a membrane which did not contain a significant amount of the enzyme. The membranes of these biosensors served primarily as a physical barrier which, by virtue of their small pore size, prevented the enzyme from migrating into the bulk solution. The membrane also served to keep large protein molecules from entering the aqueous enzyme solution and interfering with planned reactions. These biosensors were comparatively large and their reaction times were slow by modern standards.

An improved type of biosensor having a laminated membrane was sometimes employed which held an enzyme trapped between two or more individual membranes. The enzyme could be dispersed in an adhesive which held the membranes in place, especially when the enzyme was glucose oxidase and the adhesive was glutaraldehyde. The membranes did not contain a significant amount of enzyme.

A more recently developed type of biosensor contains enzymes immobilized directly within a permeable or semipermeable carrier membrane. The enzyme may be physically encapsulated within the membrane in the form of fine droplets dispersed in a polymer. Alternately, the enzyme may be covalently bonded to functional polar groups which are attached to a synthetic polymer membrane. The immobilized enzyme membranes contain micropores which facilitate diffusion of target reagents and reaction products through the membranes.

Covalent bonds for immobilizing proteins are formed by linking amino or carboxyl groups, which are present in every enzyme, with polar functional groups which may be present on the carrier membrane. The functional groups can be derived from components normally present in the material that forms a carrier substrate or the functional groups can be added to the carrier substrate. Suitable functional groups include carboxyl groups, amino groups, sulfonic acid groups, imino groups, thio groups, hydroxyl groups, pyridyl groups, and phosphoryl groups. The functional groups may be pre-activated by chemical treatment to enhance their ability to join with the amino or carboxyl groups present in the enzyme molecules.

As biosensor technology progressed, laminated membranes were produced which included an enzyme membrane which carried immobilized proteins and other membranes. The other membranes are located on one or both sides of the enzyme membrane and serve to impede the movement of undesirable species. For example, protecting membranes having relatively large pores are included in laminated membranes between an analyte solution and an enzyme membrane. In that position, the protecting membranes prevent high molecular weight species from becoming adsorbed upon and fouling the surface of the enzyme membrane. Similarly, blocking membranes with relatively smaller pores were included between the enzyme membrane and a sensing electrode to prevent low molecular weight species, such as ascorbic acid and paracetamol, from interfering with electrical detection and measurement at the sensing electrode. Some of the laminated membranes are prepared by the technique of spin casting successive layers of polymeric material.

The laminated membranes are not entirely satisfactory, however. They are expensive and time-consuming to prepare. Achieving a uniform distribution of enzyme attachment within the enzyme membrane is problematic. In addition, the laminated membranes frequently leak at their point of attachment to a sensor device and an analyte solution is then able to bypass the enzyme. Laminated membranes can also separate during operation.

Accordingly, improved laminated membranes and improved methods of manufacturing have been sought, as well as substitutes. One substitute is a blocking layer deposited directly upon the sensing electrodes. Such blocking layers are produced by polymerizing compounds directly on the electrodes, such as diaminobenzene and dihydroxybenzene copolymers. Intimate contact is achieved between the sensing electrode and the blocking membrane, but the quality of devices produced by this technique is often inconsistent.

Over the last two decades, evolution in biosensor design has been stimulated by a demand for smaller, faster, and more reliable leak-proof sensors which exhibit high sensitivity. Such sensors are especially useful for constructing arrays which contain many sensors. The demand for small biosensors with faster response and recovery times is at odds with the requirements of leak-proof reliability and high sensitivity. Generally, the route to faster response times is by incorporation of more sophisticated, less diffusion-resistant membranes, and through improved immobilization techniques which uniformly distribute the enzyme in well-defined layers without exposing the enzyme to conditions which might cause it to denature.

In contrast, the use of sophisticated laminated membranes and advanced enzyme mobilization techniques places a premium on the integrity of a seal between the enzyme membrane and the housing. Previously, the seal had been made using clamps, mechanical fasteners, or adhesives, and was a frequent source of leakage. Leakage around the enzyme would reduce the sensitivity of the biosensor device because some reagents had not been converted and, therefore, would not register at the electrode. Of course, the leakage bypass problem is most critical for small biosensor devices where the deleterious effect of any size leak becomes relatively more important. When the seal leaks, the time required to rinse out a sample or calibrant solution is extended. Undesirable species may infiltrate the sensor and interfere with detection. Avoiding leaks is especially important in the case of systems with multiple sensors.

BRIEF SUMMARY OF THE INVENTION

The present invention is directed to a biosensor device which exhibits relatively fast response and recovery times as compared to previous devices while maintaining high sensitivity and reliability. The new biosensor device employs a composite membrane that contains a porous membrane having selective molecules of a biologically active material, such as enzymes, antibodies, enzyme co-factors, and nucleic acid derivatives, that react selectively with an analyte to produce products which are detected electrically by a sensing electrode. The composite membrane incorporates at least one other membrane, which can be a blocking membrane or a protecting membrane. A blocking membrane prevents low molecular weight interfering species from reaching the sensing electrode. The blocking membrane is an integral part of the composite membrane, being at least partly embedded in pores of the porous membrane. A protecting membrane is an ultrafiltration membrane which is welded into a position where it covers the porous membrane and prevents relatively large species, such as proteins, from contacting the porous membrane. The present invention also provides a simple and effective method for manufacturing the composite membrane.

Good control over the attachment and distribution of the protein molecules is achieved by immobilizing the protein directly on the porous membrane, preferably by covalent attachment to pre-activated functional sites on the porous membrane. The protein may be immobilized either before or after the porous membrane is assembled within a housing of the biosensor device.

A permanent leak-proof connection between the enzyme membrane and the housing is achieved by welding the membrane to the housing through application of ultrasonically induced heat. The biologically active enzyme within the membrane is not denatured by such ultrasonic welding and the selectivity enhancement of the blocking layer is not disrupted.

In addition to the porous membrane containing immobilized protein molecules and the partly embedded blocking membrane, the composite membrane may optionally contain a protective membrane installed close to and substantially parallel with an external surface of the housing so as to present a simple profile to sample stream flow. The simple flow profile minimizes dead volume and backmixing of the sample, making the device suitable for use in a semi-automatic analyzer having programmed flow switching or for use within the human body. The protecting membrane also serves as an ultrafilter to prevent undesirable high molecular weight species from fouling the porous membrane which contains the immobilized protein.

The composite membrane is securely attached to the housing by ultrasonic welding, without such mechanical fastenings as O-rings or strength-reducing adhesives. The device can be reproducible constructed in extremely small sizes that minimize diffusion path lengths and contribute to quick response and rapid signal recovery for one sensor or an array of sensors.

In one embodiment, the device comprises an electrically insulating housing which defines a first aperture, a second aperture, and a passage that extends from the first aperture through the housing to the second aperture. The housing is impervious to an analyte solution that contains a reagent selectively catalyzed by a biologically reactive material, such as a protein. The device also comprises means for conducting electrical current which extend through the first aperture into the passage and seal against the first aperture in a manner that prevents fluid flow.

A composite membrane is located across the passage and ultrasonically welded to the housing such that the solution must pass from the second aperture through the enzyme membrane to contact the means for conducting electrical current. The composite membrane has a co-extensive porous membrane having an internal surface which defines a plurality of micropores distributed throughout the porous membrane. A biologically active material is immobilized within the micropores of the porous membrane. The composite membrane also includes a blocking membrane which is partly embedded within the porous membrane.

In another embodiment, the invention is a reusable biosensor device for measuring the concentration of protein catalyzed reagent in solution. The device comprises an electrically conducting pin having one or more side surfaces, a transmitting surface, and a receiving surface. An electrically conductive organic matrix may, optionally, coat the receiving surface of the pin. Covering the side surfaces and extending beyond the side surfaces is a non-porous electrically-insulating housing which is impervious to the solution. The housing defines a well that is adjacent the receiving surface and contains an ionophore gel.

A composite membrane is welded to the housing so that the composite membrane, the housing, and the receiving surface completely surround the ionophore gel. The solution must pass through the composite membrane to contact the ionophore gel.

The composite membrane includes a porous membrane which is substantially co-extensive with the composite membrane. The porous membrane is welded directly to the housing. Proteins are immobilized within the micropores of the porous membrane.

A substantially planar protecting membrane covers the porous membrane and presents a simple flow profile to the solution. The protecting membrane may be welded to the porous membrane or, alternatively, welded directly to the housing.

In yet another embodiment, the invention is a device for measuring the concentration of an enzyme-catalyzed reagent. The device comprises an electrically conductive pin. A receiving surface of the pin collects electrical information which is indicative of the concentration of the reagent in solution. The receiving surface may, optionally, be coated by a non-metallic electrical conductor, preferably a layer of graphite ink. The sides of the pin are hydraulically sealed against a thermoplastic polymer molded housing which is disposed about the pin.

The housing defines a well over the receiving surface. A composite membrane containing an immobilized enzyme membrane abuts the housing and extends across the well, while the well is substantially filled with an ionophore gel. The enzyme membrane is not welded to the housing. A substantially planar protecting membrane, which is larger in surface area than the enzyme membrane, extends over and covers the enzyme membrane, trapping the enzyme membrane in place against the housing. The protecting membrane is a part of the composite membrane. The protecting membrane is ultrasonically welded directly to the housing.

In another form, the invention is a method of manufacturing a composite membrane which is simple, reliable and eminently suited for mass production. A polymer solution containing a dissolved blocking polymer and a first solvent is provided. The blocking polymer is cellulose acetate, silicone rubber, methyl methacrylate, or a perfluorosulfonic acid polymer.

The polymer solution is placed on the surface of a forming solution containing predominantly a second solvent which is inert to the blocking polymer. In this manner, a blocking polymer film is produced which is subsequently lifted from the surface on a porous preactivated membrane.

Essentially all of the first and second solvents are evaporated from the film to produce a solid blocking polymer membrane. The blocking polymer membrane, when solidified, remains partly embedded in pores of the pre-activated membrane. The pre-activated membrane is treated with a protein solution, attaching a protein to pre-activated functional groups within the pre-activated membrane, to produce an immobilized protein membrane in which the blocking polymer membrane is partly embedded. Alternatively, the membrane with immobilized enzyme is used to lift off the blocking membrane.

DETAILED DESCRIPTION OF THE PREFERRED EMBODIMENTS

The present invention provides a biosensor device including a composite membrane attached to a housing by a leak-resistant ultrasonic welding process. The composite membrane includes a porous membrane carrying an immobilized protein and at least one other membrane. The other membrane may be a blocking membrane which is partly embedded in the porous membrane. The other membrane may be a protecting membrane, located between the porous membrane and a contemplated analyte. The invention also provides a method for manufacturing the composite membrane.

Figure 1:
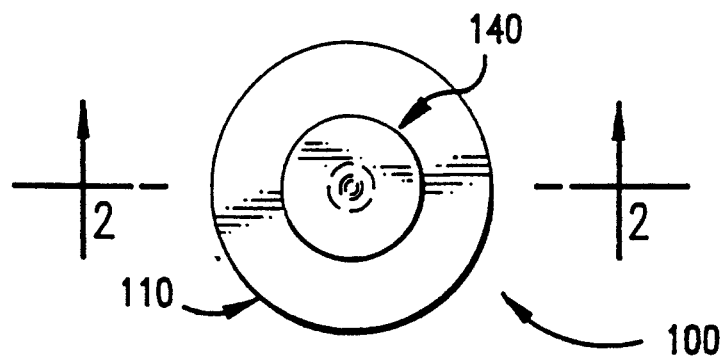
FIG. 1 is a plan view of an embodiment of the present invention.
Figure 2:
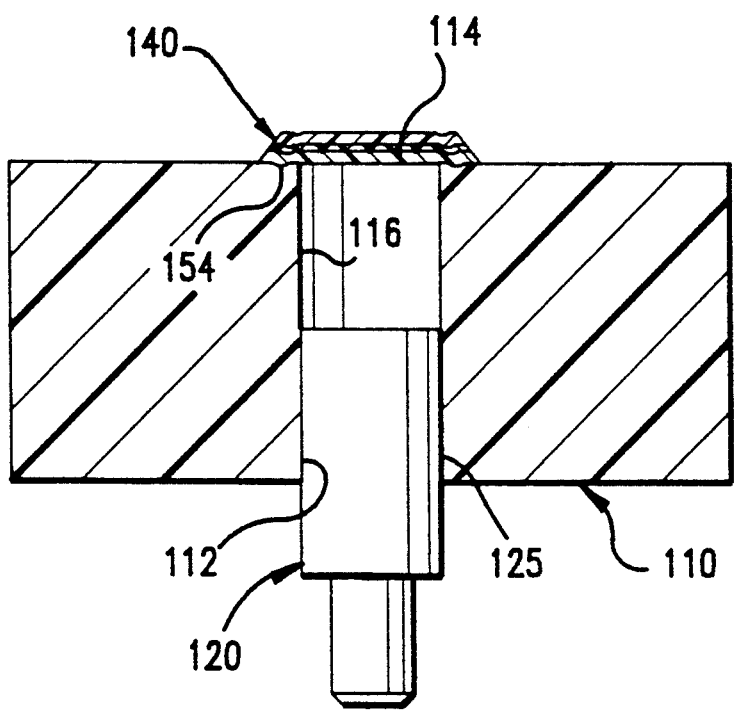
FIG. 2 is an enlarged cross-sectional view taken along the plane 2—2 in FIG. 1.
Figure 3:
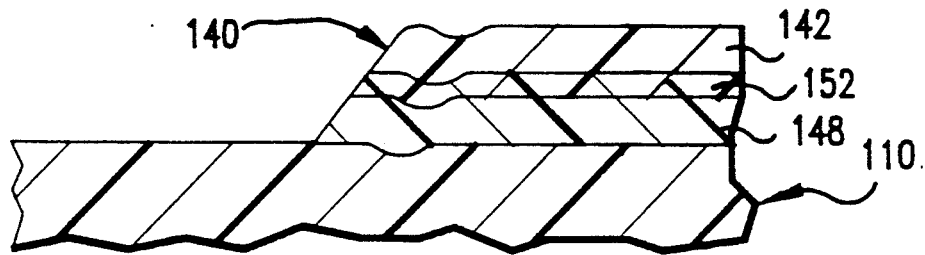
FIG. 3 is a much enlarged fragmentary cross-sectional view taken along the plane 2—2 in FIG. 1.

FIGS. 1 through 3 illustrate a device 100 which is a preferred embodiment of the present invention. FIG. 1 is a plan view of the device 100 showing a housing 110.

The housing 110 of the device 100 is impervious to a solution to be analyzed and is electrically insulating. It is preferred that the housing 110 be constructed of a thermoplastic polymer such as polyethylene, acrylonitrile butadiene styrene (ABS), polyvinyl chloride (PVC), cellulose acetate butyrate (CAB), vinylidene chloride, fluorocarbons, polycarbonates, polypropylenes, nylons, and acetals. Especially preferred are Zylar 90 TM and acrylics in general. Zylar 90 TM is a methyl methacrylate butadiene styrene terpolymer produced by Polysar of Madison, Conn. These thermoplastic polymers can be injection molded around solid conductors, metallic and otherwise, to produce a conductor-to-housing seal which is durable and highly leak-proof.

Referring now to FIG. 2, the housing 110 has a first aperture 112 and a second aperture 114 on its external surface which are connected by an internal passage 116. A means for conducting electrical current 120 is partially inserted into the first aperture 112 to lead an electrical signal from the passage 116 through the housing 110 to a point outside. There, the electrical signal can be picked up by a sensing lead (not shown) and further analyzed. Because the passage 16 is filled with an analyte solution during operation, it is important that the housing 110 be electrically insulating and that the means for conducting electrical current 120 passing through the first aperture 112 make a tight liquid seal 125 against the housing 110. Otherwise, the analyte solution might flow toward a sensing lead (not shown) and other peripheral equipment. In most cases, the seal 125 produced by injection-molding will be sufficient.

A composite membrane 140 is located across the passage 116 and ultrasonically welded to the housing 110 such that the analyte solution must pass to the second aperture 114 through the composite membrane 140 in order to contact the means for conducting electrical current 120. The composite membrane is composed of two or more constituent membranes. The composite membrane has a surface area equal to or larger than that of the cross-sectional area of the passage 116, as measured on a plane where the passage 116 meets the composite membrane 140.

As depicted in FIG. 3, the composite membrane 140 includes a porous membrane 142 which is approximately coextensive with the composite membrane 140. The porous membrane 142 is substantially in the form of a flat sheet. It is preferred that the porous membrane 142 is a portion of a semipermeable membrane made from synthetic polymer material disposed in a thin, flexible layer.

The porous membrane 142 may be composed of any chemically inert solid which possesses a large internal surface and a number of internal micropores. The micropores of the porous membranes need not be cylindrical in shape. The invention is applicable to porous membranes having micropores which are tortuous or sponge-like in shape. Nitrocellulose, polyamide, and polyvinylidene difluoride membranes can be used.

The porous membrane 142 is made from polyamide resins. Copolymers of hexamethylene diamine and adipic acid (Nylon 66), copolymers of hexamethylene diamine, and sebacic acid (Nylon 610), and homopolymers of poly-E-caprolactam (Nylon 6) are preferred. However, excellent results have been obtained with a polyvinylidene difluoride pre-activated membrane. In a typical process for manufacturing the porous membrane 142, the polyamide resin is dissolved in a solvent such as formic acid and a non-solvent such as water is added under controlled conditions of agitation to achieve nucleation of the solution. The nucleated solution is then cast onto a solid sheet or web in the form of a film. This film is contacted and diluted by a liquid non-solvent system. The polyamide resin thereupon precipitates forming a membrane sheet which can be washed to remove the solvent liquid. The membrane can then be stripped from the solvent sheet to produce the porous membrane 142. Alternatively, if the sheet is porous it can be incorporated in the porous membrane 142 to serve as a permanent support.

Commercially available non-porous membranes are preferred. Especially preferred is a commercially available pre-activated polyvinylidene difluoride membrane which is sold under the tradename Immobilon AV Affinity Membrane by Millipore of Waltham, Mass.

The most useful porous membranes are those which have a pore size in the range of about 0.01 micron to about 10 microns, where a micron is defined as $1 \times 10^{-6}$ meter. A pore size in the range of about 0.1 to about 2 microns is especially preferred. In practice, the porous membrane 142 containing immobilized enzyme is utilized in tandem with one or more other membranes.

The porous membrane 142 also includes a protein immobilized within the micropores. The protein contains peptide chains composed of a large number of amino acid derivatives, each linked to adjacent acid derivatives through a carboxyl group on one side and an amine group on the other. The peptide chains are wrapped or coiled into distinctive shapes which enhance the catalytic selectivity of the enzymes toward specific reagents. Enzymes are a subclass of proteins.

Antibodies are another subclass of proteins. Each antibody molecule is made up of four peptide chains joined by disulfide bonds into a generally Y-shaped molecule. Antibodies, also called immunoglobulins, are produced by B cells as a primary immune defense. Each antibody has a unique binding site that can combine with a complementary site of a foreign antigen.

Virtually any enzyme or antigen can be immobilized within the porous membrane 142. Examples of enzymes that may be covalently bonded are glucose oxidase, urease, creatinine deiminase, alcohol oxidase, glutamate oxidase, lysine oxidase, leucine dehydrogenase, sarcosine oxidase, creatinine amidohydrolase, creatinine amidinohydroxolase, trypsin, glutamate dehydrogenase, lactate dehydrogenase, and hexokinase. Good results have been obtained with glucose oxidase, urease, and creatinine deiminase. The nature of the analyte will dictate which enzymes or antigens are utilized.

Several means of immobilizing enzymes and antibodies on the porous membrane 142 are known, such as adsorption, entrapment, ionic, and covalent bonding. Any such method which does not denature the enzyme or antibody can be used in the present invention. Covalent bonds that immobilize enzymes are formed by linking amino groups or carboxyl groups, which are present in every enzyme, with polar functional groups attached to the porous membrane 142. The functional groups can be derived from components normally present in the material that forms a substrate of the porous membrane 142 or the functional groups can be added to the substrate. Suitable functional groups include carboxyl groups, amino groups, sulfonic acid groups, imino groups, thio groups, hydroxyl groups, pyridyl groups, and phosphoryl groups. The functional groups may be pre-activated by chemical treatment to enhance their ability to join with the amino or carboxyl groups present in the enzyme molecules.

It is preferred that the porous membrane 142 have functional groups which are pre-activated. An Immobilon TM membrane obtained from Millipore of Waltham, Mass., and an Immunodyne TM membrane obtained from Pall Corporation of Glen Cove, N.Y., are examples of suitable commercially-available pre-activated membranes.

The shape of the coiled polypeptide chain which forms the enzyme or the antibody is critical to its function as an organic catalyst. Many, if not all, enzymes and antibodies are shape-selective. That is, they recognize specific reagents which have shapes that complement the shape of the coiled peptide chain. If the peptide chain becomes uncoiled or changes its shape and loses its specificity toward certain reagents, the protein is said to be denatured. To avoid denaturing the protein, it is necessary to avoid subjecting the protein to extreme heat or cold, to gross changes in pH, to harsh chemicals, and to dehydration. In many cases, it is desirable to keep biologically active proteins in contact with an aqueous liquid phase at all times.

Additionally, when choosing a method of attachment for the porous membrane, harsh chemicals and chemicals which fail to wash freely from the substrate should be avoided in order to minimize the possibility of such chemicals later denaturing the enzyme. One of the surprising features of the instant invention is the discovery that porous membranes containing active immobilized proteins can be ultrasonically welded without materially denaturing the proteins.

A blocking membrane 148 is another constituent of the composite membrane 140. The blocking membrane 148 is a membrane installed between the porous membrane 142 and the means for conducting electrical current 120 which is adapted to screen out chemical species that might interfere with an intended electrical signal. The blocking membrane 148 is located so as to cover the passage 116. The blocking membrane 148 has relatively few and relatively small pores and is, therefore, capable of preventing relatively low molecular weight compounds from reaching the means for conducting electrical current 120. For example, a non-porous cellulose acetate membrane can prevent ascorbic acid from reaching the means for conducting electrical current 120 when the desired reaction product is gluconolactone and an intended electrical signal is carried by hydrogen peroxide. Hydrogen peroxide from the oxidation of glucose passes freely through the cellulose acetate membrane.

It is preferred that the blocking membrane 148 be in contact with the means for conducting electrical current 120, unless an ionophore gel is interposed. If no ionophore gel is present the length of the passage 116 is preferably minimized to hasten biosensor response and recovery.

The composite membrane 140 is ultrasonically welded to the housing 110. Ultrasonic welding produces a reliable seal 154 which prevents the analyte solution from bypassing the composite membrane 140. In the case of a circular membrane, such as the composite membrane 142, a circumferential edge of the membrane should be welded to the housing. Alternately, the entire periphery of a membrane which is not circular should be welded to the housing. The term "welding" as applied here to a thermoplastic material is intended to encompass dielectric welding, high-frequency welding, hot-gas welding, induction welding, and ultrasonic welding. Of these, ultrasonic welding is preferred.

Basically, ultrasonic welding involves converting standard electrical energy at 50 or 60 cycles per second into mechanical energy of approximately 20,000 or 40,000 cycles per second. Methods of accomplishing this conversion are well known. The mechanical energy is transferred to a horn. For this purpose, a horn is defined as a metal element which is shaped to fit closely against a surface of one of two or more items which are to be welded together. As the surface pressed against the horn vibrates in response to high-frequency mechanical energy, other surfaces of the item are firmly held to prevent movement. A portion of the item between vibrating and non-vibrating surfaces flexes at a high cyclic rate and generates heat through internal friction which melts the portion of the item in a controlled manner. When the desired melting has occurred, the flow of mechanical energy is stopped and the melted parts are allowed to cool and solidify. The horn may, optionally, be shaped to mechanically cut away excess portions of membrane at the end of the welding process.

In accordance with the present invention, it is highly desirable to employ an energy director during the ultrasonic welding in order to limit the amount of energy transferred to the means for conducting electrical current 120. An energy director is a triangular projection which is either added to the item being welded or to the horn itself which focuses mechanical energy, particularly into one small area of a joint. The excess melted material from this one small area can flow uniformly around the periphery of the joint and produces a superior weld without unnecessarily interfering with the previously existing seal 125 between the housing and the conducting means 120.

In the absence of a welding process such as one of those described above, it is possible to attach a membrane to the housing by means of a solvent cement adhesive. For particular combinations of housing material and membrane material, such a solvent cement attachment may result in an acceptable weld. However, in the majority of cases, the application of solvent cement to thermosetting plastic material will produce an unacceptably weak bond. For instance, Teflon, which is a possible choice for the housing 110 of the present invention, has no acceptable solvent cement. On the other hand, acrylic plastics are known to have effective solvent cements, such as tetrahydrofuran methylene chloride and ethylene dichloride, and may be used to reliably attach polyamide membranes to polyacrylate housings by the solvent cementing process.

In assessing the suitability of such solvent cementing techniques, one must consider the material of both the housing 110 and the composite membrane 140. Where a reliable solvent is not known, ultrasonic welding is the recommended and preferred attachment procedure.

The blocking membrane 148 has a portion 152 which is embedded within the micropores of the porous membrane 142. The portion extends over one surface of the porous membrane 142, covering an area of the porous membrane 142 which is equal to or larger than the cross-sectional area of the passage 116. The portion 152 does not extend completely through the porous membrane 142, but rather extends from the surface of the porous membrane 142 to a substantially uniform depth within the membrane. In the portion 152, micropores defined by the porous membrane 142 are filled with the blocking polymer which composes the blocking membrane 148. In this manner, a portion 152 of the blocking membrane 148 is embedded within the porous membrane 142.

The embedded portion 152 represents an advance over prior art blocking membranes. By providing intimate contact between the porous membrane 142 and the blocking membrane 148, the present invention minimizes the diffusion resistance encountered by the analyte. Essentially, no dead volume of liquid exists between the porous membrane 142 in the blocking membrane 148 which might lengthen response and recovery times. Additionally, the embedded portion 152 resists separation during use of the device. There is less chance that the analyte solution can bypass either the porous membrane 142 or the blocking membrane 148 when they are joined by the embedded portion 152. The embedded portion 152 may be relatively thin and still provide significant advantages. The two membranes join together to form a single mechanical unit.

The embedded portion 152 is most conveniently formed by lifting a film from a polymer solution containing a blocking polymer dissolved in a solvent from the surface of a liquid which is a poor solvent for the blocking polymer. The blocking polymer is selected from the group consisting of cellulose acetate, silicon rubber, methyl methacrylate and perfluorosulfonic acid polymers. Because the blocking polymer film is lifted from the liquid surface on a porous membrane, such as porous membrane 142, the film is in a fluid or semiplastic state which allows the film to enter micropores of the porous membrane 142. Subsequently, the blocking polymer film is dried and a blocking membrane 148 which is permanently embedded in the porous membrane 142 is formed.

Figure 4:
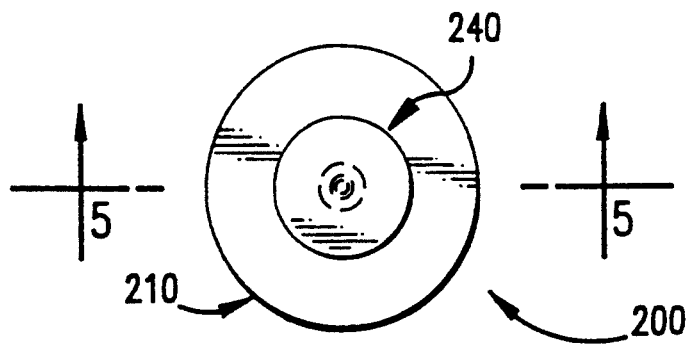
FIG. 4 is a plan view of a second embodiment of the present invention.
Figure 5:
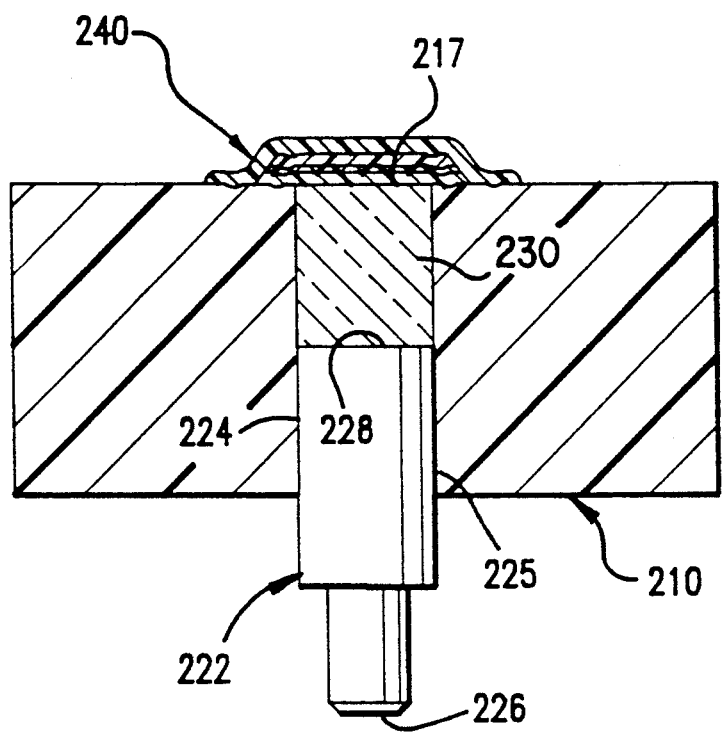
FIG. 5 is an enlarged cross-sectional view taken along the plane 5—5 in FIG. 4.
Figure 6:
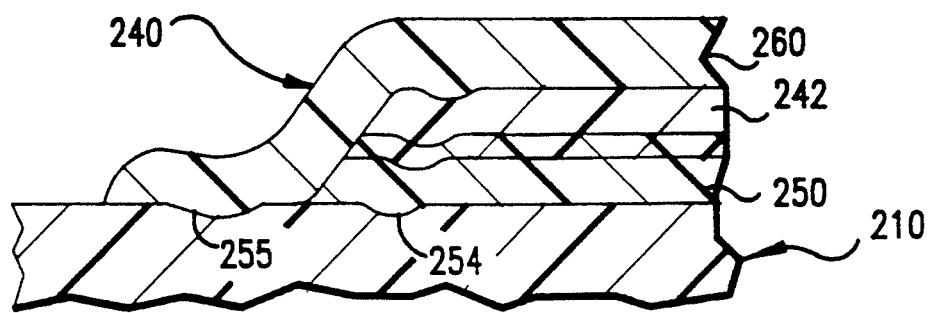
FIG. 6 is a much enlarged cross-sectional view taken along the plane 5—5 in FIG. 4.

A second embodiment of the invention is illustrated in FIGS. 4 through 6. Elements which are equivalent to those depicted in FIGS. 1 through 3 are designated by an element number which is one hundred units higher than that of the corresponding element number employed in FIGS. 1 through 3. FIG. 4 shows a device 200 having a housing 210 of generally cylindrical shape. FIG. 5 depicts an enlarged cross-sectional view of the device 200 taken along the plane 5—5 of FIG. 4.

Referring now to FIG. 5, the reusable biosensor device 200 includes a pin 222 composed of an electrically conducting material. Materials other than metals, such as carbon rods, have been used for similar service, but metal conductors appear to provide superior results when the device 200 is small in size.

The pin 222 has two active surfaces. A transmitting surface 226 is adapted to pass an electrical signal to other equipment (not shown). The other active surface is a receiving surface 228 that is adapted to receive an electrical signal. The receiving surface may, optionally, be coated with a layer of graphite ink (not shown). The electrical signal may be in the form of a change in current during a period when substantially constant voltage is maintained across the device. Alternatively, the signal may be a difference in electrical potential. Side surfaces 224 which contact or face the housing 210 are not intended to be active surfaces and merely serve to make a liquid seal 225 against the analyte solution.

The housing 210 is non-porous, electrically insulating, and impervious to the analyte solution. The housing 210 covers only the side surfaces 224 and extends beyond the side surfaces 224 to define a well 217 that is adjacent to the receiving surface 228. The housing 210 is injection-molded in place around the pin 222 to make the liquid seal 225.

An ionophore gel 230 is located within the well 217. A composite membrane 240 is disposed across the well 217 so that the composite membrane 240, the housing 210, and the receiving surface 228 completely surround the ionophore gel 230. The ionophore gel 230 assists a migration of ions to the receiving surface 228. The ionophore gel 230 completely covers the receiving surface 228 and is also in contact with the compressed membrane 240.

Whether the inclusion of an ionophore gel layer is necessary depends on the particular catalyzed reaction products which are expected to form within the membrane. As an illustration, when the immobilized enzyme is glucose oxidase and the reagent is glucose, hydrogen peroxide will be produced which needs no assistance in migrating to a surface where it can be oxidized. In contrast, when the immobilized enzyme is urease acting upon a molecule of urea to produce one molecule of carbon dioxide and two ammonium ions, the presence of an ionophore layer containing an ionophore such as nonactin is essential. Other examples of useful ionophores are valinomycin to facilitate the transport of potassium ions, nonensin to facilitate sodium ion transport, and tridodecylamine to facilitate the transfer of hydrogen ions.

When an ionophore is employed, it is preferred that the ionophore be present in the form of a gel, such as the ionophore gel 230. An example of a useful ionophore gel is the gel containing about 1.5 weight percent nonactin, about 23 weight percent polyvinyl chloride, and about 75.5 weight percent dibutyl sebacate. This particular gel is conveniently applied when dissolved in tetrahydrofuran solvent. The solvent may be removed by simple drying. Dibutyl sebacate acts as a plasticizer for the gel, allowing it to be built up in the form of a thin flexible membrane. The ionophore gel 230 may be built up by performing multiple application and drying steps.

The composite membrane 240 includes a porous membrane 242 which is substantially coextensive with the composite membrane. The porous membrane 242 has a larger surface area than the cross-sectional area of the well 217, as measured at a point where the composite membrane 240 meets the well 217. The porous membrane 242 has an internal surface which defines micropores. An enzyme is immobilized within the porous membrane 242 as described above.

Referring now to FIG. 6, the porous membrane 242 is ultrasonically welded to the housing 210 making a liquid-tight seal 254 with the housing 210. A protecting membrane 260 which is larger in area than the composite membrane 240 is disposed over the composite membrane and is ultrasonically welded directly to the housing 210 to produce a liquid seal 255 at a slight distance from the liquid seal 254. The composite membrane 240 also contains a blocking membrane 250, adjacent to the housing.

The protecting membrane 260 is adapted to prevent high molecular weight interfering compounds from reaching the porous membrane 242 and to protect the porous membrane 242 from contact with any particulate foulant which may be present in the analyte solution. Polycarbonate is a preferred material for the protecting membrane 260. As an illustrative example, the protecting membrane 260 which has a thickness of about 8 microns and micropores having an effective pore diameter of approximately 300 Å is favored for sampling the urea content of a spent dialysate produced by peritoneal dialysis. Other dimensions may be more suitable for other specific applications.

The composite membrane 240 is in the form of a relatively thin sheet, preferably having a thickness in the range of about 20 to about 300 micrometers. The composite membrane 240 is conveniently assembled after enzyme has been immobilized within the porous membrane 242. Preferably, the enzyme is immobilized within the porous membrane 242 in a substantially uniform distribution. Urease and deiminase are preferred enzymes for immobilization within the porous membrane 242.

Figure 7:
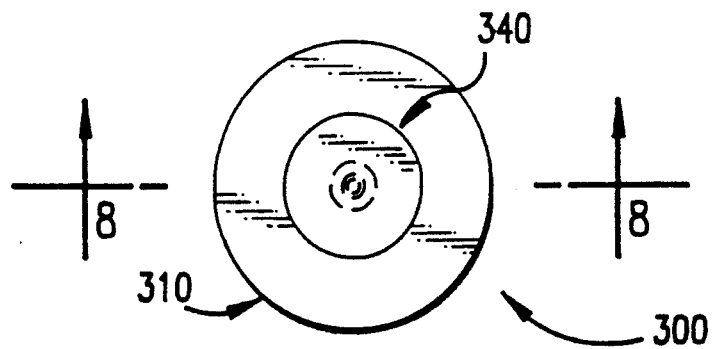
FIG. 7 is a plan view of a third embodiment of the present invention.
Figure 8:
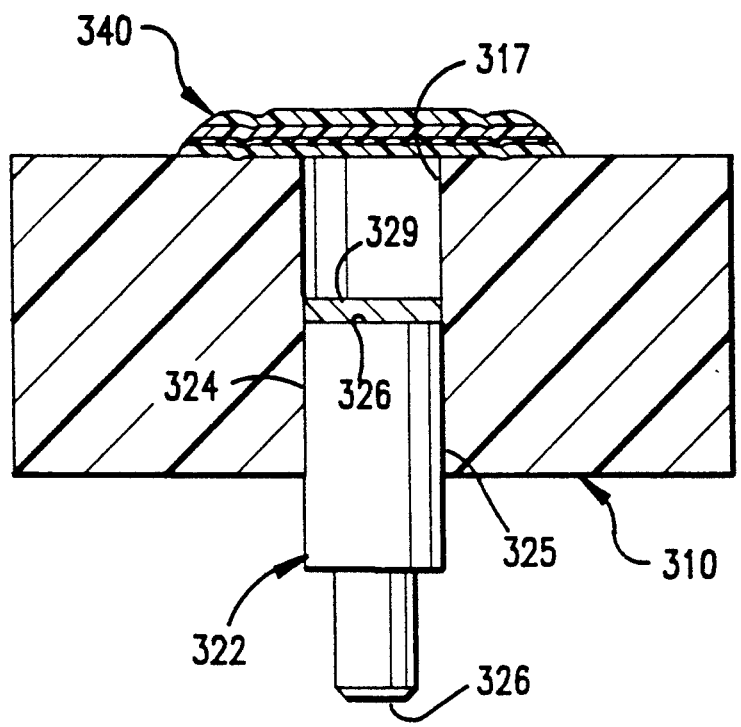
FIG. 8 is an enlarged cross-sectional view taken along the plane 8—8 in FIG. 7.
Figure 9:
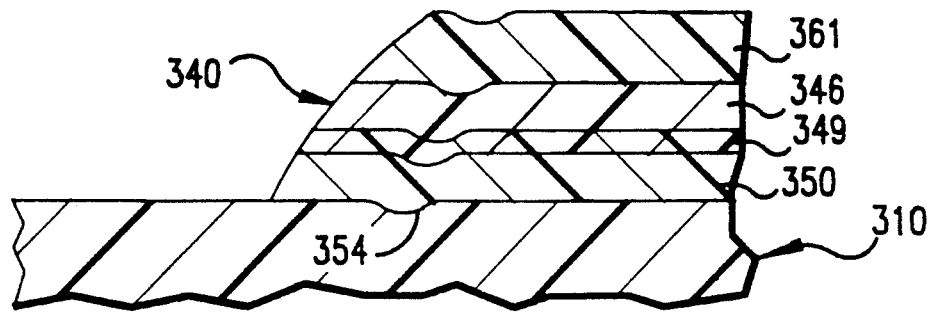
FIG. 9 is a much enlarged cross-sectional view taken along the plane 8—8 in FIG. 7.

FIGS. 7 through 9 illustrate a device 300 which also embodies the present invention. FIG. 7 is a plan view of the device 300. FIG. 8 is an enlarged cross-sectional view of the device 300 as taken along plane 8—8 of FIG. 7.

Referring now to FIG. 8, the device includes a pin 322 which is composed of an electrically conducting material and has a side 324 and a receiving surface 326. The receiving surface 326 is coated with a layer of graphite ink 329.

A recurring problem in electrochemical sensor devices having a metallic conductor is corrosion of the conductor by the electrolytic sample solution. The present invention may, optionally, overcome this difficulty through physically isolating the pin 322 from the analyte solution by interposing a layer of carbonaceous material, such as the layer of graphite ink 329. The layer of graphite 329 may be screen-printed or painted upon the pin 322. Many forms of carbon are suitable for this application. One example of a suitable graphite ink is a flexible carbon keyboard contact ink offered by Minico Inc. under the tradename M-3000-RS.

The layer of graphite ink 329, if present, must completely cover the receiving surface 326 which would otherwise be exposed to the analyte solution. The layer of graphite ink 329 may also coat other surfaces of the pin. For example, one might dip an entire end of the pin 329 into a pool of graphite ink to be sure that the receiving surface 326 was fully coated. For the purposes of the present invention, a portion of the layer of graphite ink 329 may extend over the side 324 of the pin and still be within the scope of the claims. If a carbonaceous coating, such as the graphite layer 329, is not employed the pin 322 should be composed of or plated with corrosion resistant materials such as platinum, palladium, or gold.

The present invention may advantageously employ a modified graphite layer which coats a receiving surface, such as the receiving surface 326. For example, certain amperometric sensors relying on oxidation reactions to produce a detectable signal may incorporate thiazine dyes, such as Meldola Blue, within the modified graphite layer. Meldola Blue can decrease the amounts of electrical potential required to oxidize enzyme co-factors, such as nicotine adenine dinucleotide phosphate (NADPH).

The device 300 also includes a thermoplastic polymer-molded housing 310 covering only the side 324 of the pin 322 and extending beyond the receiving surface 326 so as to define a well 317 over the receiving surface 326. Disposed across the well 317 is a composite membrane 340 having a polyvinylidene difluoride enzyme membrane 346, better illustrated in FIG. 9. The enzyme membrane 346 contains functional groups and also includes an immobilized enzyme which is covalently attached to the functional groups. The enzyme membrane 346 abuts the housing 310 and extends across the well 317, so that the analyte solution must pass through the enzyme membrane 346 in order to contact the receiving the surface 326. The enzyme membrane 346 is not welded to the housing.

Referring to FIG. 9, the composite membrane 340 incorporates a substantially planar ultrafiltration protecting membrane 361. The protecting membrane 361 covers the enzyme membrane 346 and is ultrasonically welded to the housing 310 making a seal 354. The protecting membrane 361 extends over and covers the enzyme membrane 346, trapping the enzyme membrane 346 in the place against the housing. The analyte solution must pass through the protecting membrane 361 to reach the enzyme membrane 346. The composite membrane 340 also contains a blocking membrane 350, adjacent to housing 310.

Figure 10:
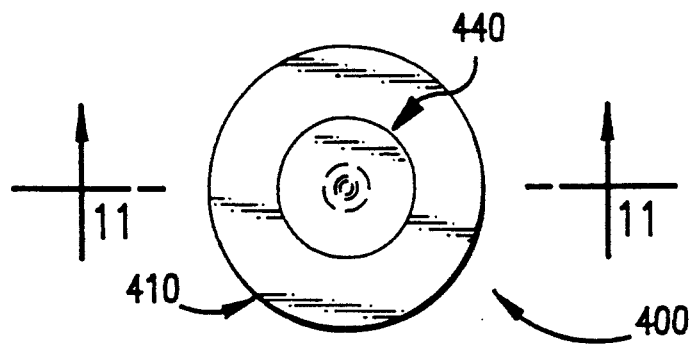
FIG. 10 is a plan view of a fourth embodiment of the present invention.
Figure 11:
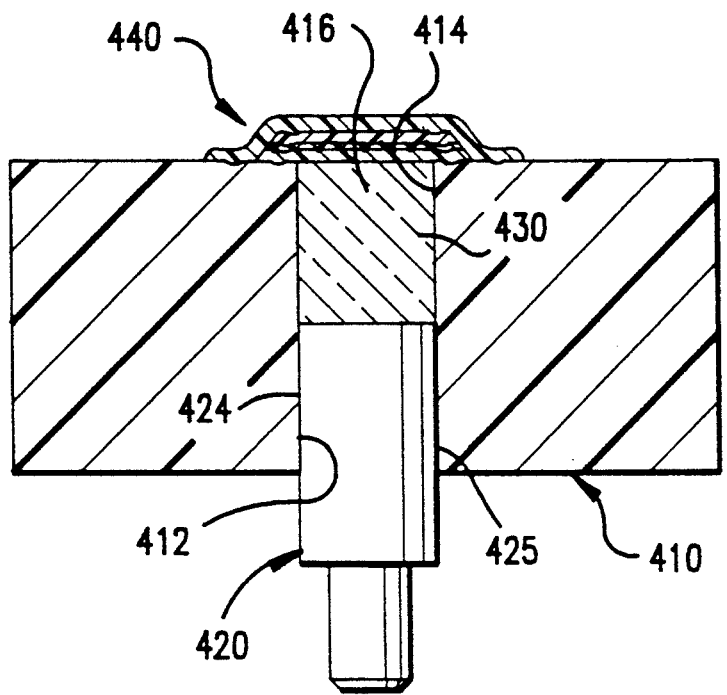
FIG. 11 is an enlarged cross-sectional view taken along the plane 11—11 in FIG. 10.
Figure 12:
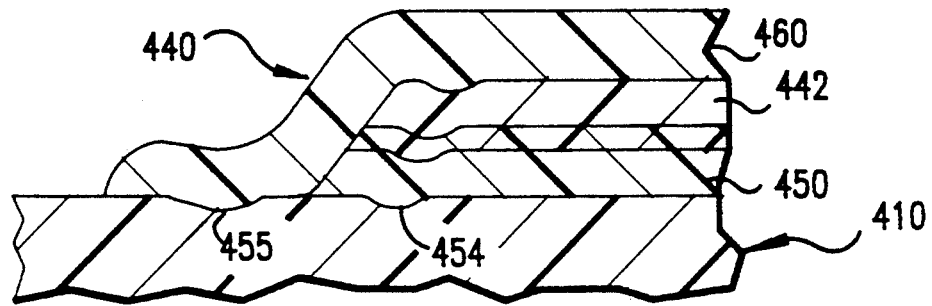
FIG. 12 is a much enlarged cross-sectional view taken along the plane 11—11 in FIG. 10.

FIGS. 10 through 12 illustrate a device 400, embodying into present invention, which is suitable for use as either an amperometric or a potentiometric sensor. FIG. 10 is plan view of the device 400 which has a housing 410. FIG. 11 is an enlarged cross-sectional view of the device 400 as taken along plane 11—11 of FIG. 10.

Referring now to FIG. 11, the device 400 includes means for conducting electrical current 420 which protrude into and substantially through a passage 416 defined by the housing 410. The passage terminates in a first aperture 412 at one end and in a second aperture 414 as the other end. The housing 410 is disposed around and fits closely to the means for conducting electrical currents 420, effecting a leak-resistant liquid seal 425.

Within the passage 416, relatively nearer to the end of the passage which terminates in the second aperture 414, an ionophore gel 430 is positioned. The ionophore gel 430 contacts the means for conducting electrical current 420 and also contacts a composite membrane 440 which abuts the housing 410 and extends across the second aperture 414. The housing 410, the means for conducting electrical current 420, and the composite membrane 440 completely surround the ionophore gel 430.

Also within the passage 416, an organic matrix, such as a layer of graphite ink, may be disposed across the passage 416 so as to prevent analyte solution which passes through the composite membrane 440 from contacting the means for conducting electrical current 420. Also, a blocking layer, composed of cellulose acetate for example, may be disposed within and across the passage 416 in a manner that prevents low molecular weight interfering species from travelling through the passage 416 to the means for conducting electrical current 420.

The composite membrane 440 includes a porous membrane 442 in which biologically active material (not shown) has been immobilized. The porous membrane 442 has a cross-section which is greater than that of the passage 416. The porous membrane 442 extends across the second aperture 414 so that the analyte solution must pass through the porous membrane 442 in order to enter the passage 416. The porous membrane 442 is ultrasonically welded directly to the housing 410.

A composite membrane of the present invention also includes at least one other membrane which may be a blocking membrane or a protecting membrane. The other membrane(s) must be attached to a housing, either directly or indirectly, by ultrasonically welding. An example of indirect attachment is a first membrane which is not welded to the housing being trapped in place against the housing by a second membrane which is ultrasonically welded in place.

Referring to FIG. 12, the device 400 includes both a blocking membrane 450 and a protecting membrane 460. The blocking membrane 450 is partly embedded within the porous membrane 442. The blocking layer 450 extends across the second aperture 414 between the porous membrane 442 and the means for conducting electrical current 420. The blocking layer 450 is ultrasonically welded to the housing, making a liquid-tight seal 454, and to the porous membrane 442.

The protecting membrane 460 is also a part of the composite membrane 440. The protecting membrane 440 abuts the housing 410 and covers the porous membrane 442. The protecting membrane 442 is ultrasonically welded to the housing 410, thereby creating a leak resistant seal 455.

In yet another embodiment, the invention a method for manufacturing a composite membrane. The method is surprisingly simple and is well suited for mass production. A large composite membrane could be manufactured by the method, tested in one piece, and then divided to produce a multitude of smaller composite membranes each of a high, authenticated quality.

A polymer solution is prepared or obtained which contains a blocking polymer. Blocking polymers are those materials which can be formed into a relatively thin homogeneous membrane that acts as a barrier to small interfering species such as ascorbic acid 4-acetamidophenol, 4-amino-2-hydroxybenzoic acid, gentisic acid, salicylamide, guaiacol, pyrocatechol, and L-$\beta$-3,4,dihydroxyphenylalanine yet allow relatively free passage to the products of catalytic protein reactions such as hydrogen peroxide and ammonium ions. The blocking polymer may be selected from the group consisting of cellulose acetate, silicone rubber, methylmethacrylate, and perfluorosulfonic acid polymers. Cellulose acetate and perfluorosulfonic acid polymers are preferred. Good results have been obtained with perfluorosulfonic acid polymers obtained under the registered trademark Nafion from the DuPont Company.

The polymer solution also contains a first solvent which serves to dissolve the blocking polymer. Cyclohexanone is recommended as the first solvent for dissolving cellulose acetate. A lower aliphatic alcohol is preferred as the first solvent when the blocking polymer is a perfluorosulfonic acid polymer.

The polymer solution is placed onto a liquid surface of a forming solution. The forming solution is composed predominantly of a second solvent that is relatively inert to the blocking polymer, thereby producing a blocking polymer film. The film is typically on the order of about 1 to about 10 micrometers thick. The temperature of the forming solution may have a significant effect upon the formation of the film. When the blocking polymer is a perfluorosulfonic acid polymer, it is recommended that the forming solution be maintained at a relatively cool temperature in the range of about 4° C. Additionally, it maybe advantageous to add a nonionic surfactant to the forming solution to minimize cracking of the film.

After the blocking polymer film has formed and is in a liquid or plastic state, the blocking polymer film is lifted from the surface of the forming solution on a semi-permeable porous pre-activated membrane. A preactivated membrane is one having covalent functional groups attached which have been previously prepared to accept biologically active proteins. Such pre-activated membranes are commercially available. A particularly favored pre-activated membrane is a pre-activated polyvinylidine difluoride membrane obtained from Millipore of Waltham, Mass. under the tradename Immobilon TM AV Affinity Membrane which contains polar functional groups and has an average pore size of about 0.65 microns. An adequate procedure for lifting the blocking polymer film is to immerse a sheet of the pre-activated membrane into the second solute under the film and raise both the film and the pre-activated membrane out of the liquid.

It is important that the forming solution be substantially inert to the blocking polymer. Otherwise, an acceptable blocking polymer film will not form. To this end, the forming solution is composed predominantly of a second solvent which is itself relatively inert to the blocking polymer. When the blocking polymer is cellulose acetate, water is recommended as the second solvent. When the blocking polymer is a perfluorosulfonic acid polymer, chloroform is preferred as the second solvent. Other solvents with a density greater than 1.0 would also be appropriate, such as carbon tetrachloride or other halogenated solvents.

After the blocking polymer film has been lifted from the forming solution it is dried by evaporation to produce a blocking polymer membrane which is partly embedded in the pre-activated membrane. Very little embedding is necessary to substantially improve ease in handling the thin, fragile blocking layer. By acting as a backing the enzyme membrane makes the blocking membrane much easier to handle.

If sufficiently volatile materials are chosen for use as the first solvent and the second solvent, the evaporation may be accomplished by drying at room temperature in an hour or less. When dry, the blocking polymer membrane is a solid which extends beneath the surface of the pre-activated membrane by way of the pores. Essentially no void volume exists between the pre-activated membrane and the blocking polymer membrane. The bond formed between the two membranes is durable.

The pre-activated membrane is treated with a protein solution to produce an immobilized enzyme membrane in which the blocking polymer membrane is partly embedded. The treating may be accomplished by applying the protein solution to a side of the pre-activated membrane opposite the blocking polymer membrane. It is preferred that the protein be attached by formation of a covalent bond. Alternatively, the enzyme can be immobilized on the membrane prior to lifting off the blocking membrane.

As a means of further disclosing the present invention, the following examples are offered. The content of the examples is not intended to limit the scope of the claims for the present invention.

EXAMPLE 1

A composite membrane was prepared having a perfluorosulfonic acid polymer as a blocking polymer and a Millipore Immobilon TM AV Affinity Membrane as a pre-activated membrane by a procedure in which glucose oxidase was immobilized upon the pre-activated membrane. The composite membrane so produced was tested for response and selectivity to hydrogen peroxide, glucose, ascorbic acid, and 4-acetamidophenol.

A polymer solution was obtained from Solutions Technology Inc. of Mendenhall, Pa., which contained 17% by weight of Nafion TM, a perfluorosulfuric acid polymer produced by the DuPont Company. The Nafion TM had a molecular weight of about 1100 and was present in the hydrogen form. Fifty microliters of the polymer solution was dropped onto a surface of a forming solution which contained 90 milliliters of chloroform and 0.5 milliliters of a nonionic surfactant. The forming solution was maintained at a temperature of approximately 4° C.

The film of Nafion TM spread out to a diameter in the range of about 1.2 to about 1.7 centimeters. The film was about 10 micrometers thick. The Millipore Immobilon TM AV Affinity Membrane was lowered into the forming solution under the Nafion TM film, then both the film and the membrane were lifted up and out of the forming solution. Chloroform was allowed to evaporate from the film and the membrane.

The membrane was mounted over a circular open end of a cylindrical electrode jacket obtained from Universal Sensors, Inc. of New Orleans, La. The membrane was mounted so that a side of the membrane having Nafion TM attached was facing to the inside of the electrode jacket.

A glucose oxidase solution was prepared by dissolving 17.14 milligrams of enzyme having an activity of 177 International Units per milligram and 3.033 milliliters of 0.5 molar potassium dihydrogenphosphate solution. The solution was adjusted to 7.5 pH.

Twenty microliters of the glucose oxidase enzyme solution was applied to the outside portion of the membrane having Nafion TM on one side. As a control test, a second Immobilon membrane was mounted on a second electrode jacket and treated with the glucose oxidase solution. The second membrane contained no Nafion TM. Both membranes were then allowed to dry at room temperature for 15 hours.

After drying, while still mounted on their respective electrode jackets, both membranes were rinsed with a buffer solution having a pH of 7.5. Then the electrode jackets were filled with a buffered saline solution having a pH of about 7.0. Each jacket was attached to a separate base platinum electrode, which was further attached to a dedicated potentiostat and a strip chart recorder. Each of the base platinum electrodes incorporated both a platinum working electrode and a reference electrode of silver coated with silver chloride. Finally, the membrane-covered electrode jackets were placed one at a time in 5 milliliter samples of stirred buffer solution and a potential of 650 millivolts was applied to the working electrode.

In separate experiments, the following test substances were added to disturb the samples of buffer solution and a rate of increase in electrical current was measured: hydrogen peroxide (0.0353 mM) glucose (5.55 mM), ascorbic acid (0.221 mM), and 4-acetamidophenol (1.184 mM). The results are presented in TABLE 1. Two trials are reported for each experiment.

TABLE 1

|  | Hydrogen Peroxide nA/min/mM | Glucose nA/min/mM | AA nA/min/mM | APAP nA/min/mM |
|---|---|---|---|---|
| Nafion TM Composite | 994, 1020 | 138, 141 | 6.3, 6.6 | 48, 49.4 |
| Immobilon TM Alone | 3994, 4164 | 501, 512 | 946, 923 | 658, 608 |

The response of the Nafion TM -Immobilon TM composite membrane to all test compounds was lower than the response of the Immobilon TM membrane without Nafion TM. Although the response to glucose indicates that active enzyme was successfully incorporated into both membranes, the selectivity of the Nafion TM - Immobilon TM composite membrane was greater than that of the Immobilon TM membrane without Nafion TM.

EXAMPLE 2

A composite membrane having cellulose acetate as a blocking polymer was prepared by a procedure in which 2.0 grams of cellulose acetate was dissolved in 50 milliliters of cyclohexanone to produce a polymer solution and a 0.25 milliliter portion of the polymer solution was dropped onto a pan of water which served as a forming solution. A thin, fragile film formed and was picked up by immersing a sheet of Immobilon TM AV Affinity Membrane in the forming solution underneath the film and raising both the film and the membrane up and out of the forming solution. Both the blocking polymer film and the membrane were allowed to dry at room temperature for 30 minutes.

A protein solution was prepared by dissolving 32.7 milligrams of glucose oxidase, having 112 International Units per milligram, and 1831 microliters of 0.5M potassium dihydrogenphosphate with a pH of 7.5. A portion of the protein solution, 915 microliters, was spread on the side of the composite membrane opposite to the side on which the cellulose acetate was attached. The composite membrane so produced was allowed to dry for 19 hours and then rinsed in buffer solution.

Two pieces of the cellulose acetate composite membrane were individually mounted on an electrode jacket from Universal Sensors, Inc., placing the cellulose acetate layer toward the inside, as described in EXAMPLE 1. The following test substances were sequentially added to the stirred buffer solution, and the rate of increase in electrical current was measured: hydrogen peroxide (0.0353 mM) glucose (5.55 mM), ascorbic acid (0.221 mM), and 4-acetamidophenol (1.185 mM). The time at which the maximum rate of current change occurred was also recorded. Results are presented in TABLE 2.

TABLE 2

| Membrane | Hydrogen nA/min/mM | nA/min/mM | nA/min/mM | nA/min/mM |
|---|---|---|---|---|
|  | (time of max. rate. seconds) | | | |
| 1 | 1615 (4) | 462 (7.5) | 5.96 (3–6) | 66.8 (13.5) |
| 2 | 1615 (4) | 162 (5) | 5.16 (2–5) | 68.4 (13.5) |

The results indicate that the cellulose acetate composite membrane responds measurably to glucose and has good selectivity for excluding ascorbic acid and 4-acetoamidophenol. The maximum rate of response for the composite membrane to glucose was very fast. The response of the composite membrane to 4-acetamidophenol was significantly slower. The difference in response rates indicates that the glucose concentration of many complex samples having response times of less than 7.5 seconds can be analyzed with essentially no interference from 4-acetamidophenol.

EXAMPLE 3

This hypothetical example will serve to illustrate how a biologically active antibody can be immobilized on internal surfaces of a compressed porous membrane and an uncompressed porous membrane. The compressed membrane is prepared by application of sufficient force to irreversibly decrease the thickness of the membrane from about 136 micrometers to 90 micrometers. One surface of the membrane is exposed to a solution of an antigen and an antigen-enzyme conjugate for a predetermined amount of time. The surface of the membrane is subsequently exposed to a rinse solution which does not contain the antigen or the antigen-enzyme conjugate. The surface is then exposed to a solution of an enzyme substrate for a fixed amount of time. The amount of reaction product from the enzyme reaction is measured with an appropriate electrode, or by use of another type of sensing element, to determine the amount of antigen.

The surface of the membrane may, optionally, be exposed to a solution of chaotropic reagent in order to disassociate the antibody-antigen and the antibody-antigen-enzyme complexes, thereby enabling the membrane to be reused.

The amount of time required for complete removal of unbound antigen-enzyme conjugate during the rinse step is chiefly determined by the time required for unbound antigen-enzyme conjugate to diffuse out of the membrane. Likewise, the amount of time required for complete removal of unbound antigen and antigen-enzyme conjugate during the chaotropic reagent regeneration step is chiefly determined by diffusion of unbound antigen-enzyme conjugate out of the membrane. Time required for diffusion is believed to be proportional to the diffusion distance squared. Compressing the membrane form 136 micrometers to 90 micrometers decreases the diffusion distance by 34% and, theoretically, decreases the time required for diffusionally related processes by 56%.

The membranes so produced contain immobilized biologically active antibodies. The membranes can be welded directly to a housing of a device according to the present invention, either with or without a protecting membrane. Alternatively, the membranes can be trapped against the housing by a protective membrane, which is welded to the housing. Blocking layers, ionophore gels, and electrically conductive graphite layers may optionally be employed with the membranes containing biologically active antibodies.

What is claimed is:

1. A device for measuring the concentration of an analyte in a solution, which comprises:
   (a) an electrically insulating housing which defines a first aperture, a second aperture, and a passage that extends from the first aperture through the housing to the second aperture and which is impervious to a solution that contains an analyte selectively catalyzed by an enzyme;
   (b) means for conducting electrical current which extend through the first aperture into the passage and are sealed against the first aperture in a manner that prevents fluid flow; and
   (c) a composite membrane located across the passage and ultrasonically welded to the housing so that the solution must pass to the second aperture through the composite membrane to contact the means for conducting electrical current, said composite membrane having
   a porous membrane which is co-extensive with the composite membrane and which includes an internal surface defining micropores;
   a biologically active material immobilized within the micropores of the porous membrane;
   a blocking membrane having a portion which is embedded in the porous membrane within the micropores; and
   a planar protecting membrane covering the enzyme membrane and ultrasonically welded to the housing.

2. The device of claim 1 wherein the porous membrane is a porous pre-activated membrane comprising a polyamide or polyvinylidine difluoride.

3. The device of claim 1 wherein a portion of the means for conducting electrical current is coated with a modified graphite layer containing a thiazine dye.

4. The device of claim 1 wherein the protein is glucose oxidase.

5. The device of claim 1 wherein the protein is urease.

6. The device of claim 1 wherein the protein is creatinine deiminase.

7. A device for measuring the concentration of an analyte in a solution, which comprises:
   (a) an electrically insulating housing which defines a first aperture, a second aperture, and a passage that extends from the first aperture through the housing to the second aperture and which is impervious to a solution that contains an analyte selectively catalyzed by an enzyme;
   (b) means for conducting electrical current which extend through the first aperture into the passage and are sealed against the first aperture in a manner that prevents fluid flow; and
   (c) a composite membrane located across the passage and ultrasonically welded to the housing so that the solution must pass to the second aperture through the composite membrane to contact the means for conducting electrical current, said composite membrane having
   a porous membrane which is co-extensive with the composite membrane and which includes an internal surface defining micropores;
   a protein immobilized within the micropores of the porous membrane; and
   a blocking membrane having a portion which is embedded in the porous membrane within the micropores.

8. The device of claim 1 wherein the porous membrane is a porous pre-activated membrane comprising a polyamide or polyvinylidine difluoride.

9. The device of claim 1 wherein the composite membrane is formed in the shape of a flat and thin sheet.

10. A reusable biosensor device for measuring the concentration of a protein-catalyzed reagent in solution, which comprises:
    (a) an electrically conducting pin having one or more side surfaces, a transmitting surface, and a receiving surface;
    (b) a nonporous, electrically insulating housing which is impervious to the solution, covers only the side surfaces, and extends beyond the side surfaces so as to define a well that is adjacent the receiving surface;
    (c) an ionophore gel inside the well; and
    (d) a composite membrane located across the well and spaced from the pin, ultrasonically welded to the housing so that the composite membrane, the housing, and the receiving surface completely surround the ionophore gel and so that the solution must pass through the composite membrane to contact the ionophore gel; said composite membrane including
    a porous membrane co-extensive with the composite membrane and having a larger surface area than the cross-sectional area of the well as measured opposite the composite membrane and having an internal surface which defines micropores;
    a protein immobilized within the porous membrane; and
    a planar protecting membrane ultrasonically welded to the housing which covers the composite membrane and presents a simple flow profile to the solution.

11. The device of claim 10 wherein a layer of graphite ink coats the receiving surface.

12. The device of claim 10 wherein the composite membrane has a thickness and in that the thickness is in the range of about 20 to about 300 micrometers.

13. The device of claim 10 wherein the composite membrane is welded to the housing after the immobilized enzyme is attached to the porous membrane.

14. The device of claim 10 wherein the immobilized enzyme is dispersed throughout the porous membrane in a uniform distribution.

15. The device of claim 10 wherein the immobilized enzyme is urease.

16. The device of claim 10 wherein the immobilized enzyme is creatinine deiminase.

17. A device for measuring the concentration of an enzyme-catalyzed reagent in a solution, which comprises:
    (a) an electrically conducting pin having a side and a receiving surface;
    (b) a layer of graphite ink which coats the receiving surface of the pin;
    (c) a thermoplastic polymer molded housing which covers only the sides of the pin and extends beyond the receiving surface so as to define a well adjacent the receiving surface;
    (d) a composite membrane disposed across the well including an enzyme membrane having functional groups, abutting the housing and extending over the well so that the solution must pass through the enzyme membrane to contact the receiving surface;

an immobilized enzyme covalently attached to the functional groups; and a planar ultrafiltration protecting membrane covering the enzyme membrane and ultrasonically welded to the housing.

18. The device of claim 17 wherein an ionophore gel is surrounded by the pin, the housing, and the composite membrane.

* * * * *